(12) United States Patent
Kuo et al.

(10) Patent No.: US 7,447,551 B2
(45) Date of Patent: Nov. 4, 2008

(54) FLEXIBLE IMPLANTABLE ELECTRICAL STIMULATOR ARRAY

(75) Inventors: Tsung Ter Kuo, Hsinchu County (TW); Kuo Hua Tseng, Hsinchu County (TW); Yu Kon Chou, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 155 days.

(21) Appl. No.: 11/146,021

(22) Filed: Jun. 7, 2005

(65) Prior Publication Data

US 2006/0149319 A1  Jul. 6, 2006

(30) Foreign Application Priority Data

Dec. 30, 2004  (TW) .............................. 93141502 A

(51) Int. Cl.
*A61N 1/04* (2006.01)
(52) U.S. Cl. .................. 607/152; 607/116; 607/117
(58) Field of Classification Search ............... 607/2, 607/115, 116; 600/508
See application file for complete search history.

(56) References Cited

U.S. PATENT DOCUMENTS

| | | | | |
|---|---|---|---|---|
| 3,717,153 A | * | 2/1973 | Bowers | 607/27 |
| 4,102,344 A | * | 7/1978 | Conway et al. | 607/17 |
| 4,837,049 A | * | 6/1989 | Byers et al. | 216/6 |
| 5,989,245 A | * | 11/1999 | Prescott | 606/14 |
| 6,038,480 A | * | 3/2000 | Hrdlicka et al. | 607/116 |
| 6,051,017 A | * | 4/2000 | Loeb et al. | 607/1 |
| 6,643,552 B2 | * | 11/2003 | Edell et al. | 607/116 |
| 2004/0059392 A1 | * | 3/2004 | Parramon et al. | 607/36 |

\* cited by examiner

*Primary Examiner*—Carl H. Layno
*Assistant Examiner*—Natasha N Patel
(74) *Attorney, Agent, or Firm*—Bacon & Thomas, PLLC

(57) ABSTRACT

A flexible implantable electrical stimulator array is provided, which is associated with a flexible circuit board, biocompatible materials, a cathode electrode array and an anode electrode array. By using the flexible circuit board, the implanting position and implanting way of the present electrical stimulator are more flexible. Hence, the present electrical stimulator is more humanized and more widely used. Besides, by a design of electrode arrays, electrical treatment area is enlarged and electrical treatment efficiency is improved.

10 Claims, 3 Drawing Sheets

FLEXIBLE IMPLANTABLE ELECTRICAL STIMULATOR ARRAY

BACKGROUND OF THE INVENTION

1. Field of the Invention

The present invention relates to an implantable electrical stimulator, and more particularly to a flexible implantable electrical stimulator using a flexible circuit board.

2. Description of the Related Art

Electrical stimulator combines theories of Chinese traditional Point Percussion Therapy and TENS (Transcutaneous Electrical Nerve Stimulation) by using finite electrical current to stimulate particular points or muscles for reaching the effects of strong and health, that is, by using electrical current with proper frequency to stimulate nerves, muscles and cells continuously and gently, which can activate the self-recovering mechanism of body. There are two kinds of therapies clinically, TENS and EMS (Electrical Muscle Stimulation).

The electrical stimulators are widely used in rehabilitation, and due to the recent breakthrough of microelectronic technique, MEMS (Micro-Electro-Mechanical Systems), biomaterial and biocompatible package technique, it makes electrical stimulators to be a miniature and implantable type.

A well-known electrical stimulator with biocompatible package encases all electrical components by a glass shell to prevent body fluid from infiltration. However, the glass package is a such hard package structure, if it is implanted into human's muscle structure, its metal materials therein will be directly contact with inner tissue of human body once it is broken due to the extrusion from muscular activities, and further releasing toxic materials, and can not achieve the purpose to be biocompatible.

SUMMARY OF THE INVENTION

It is one objective of the present invention to provide an implantable electrical stimulator employing a flexible circuit board to make the implanting position and implanting way of the present electrical stimulator more flexible. Hence, the present electrical stimulator is more humanized and more widely used.

It is a further objective of the present invention to provide an implantable electrical stimulator, which employs a design of electrode arrays to enlarge an electrical treatment area and improve electrical treatment efficiency.

It is another objective of the present invention to provide an implantable electrical stimulator, which employs flexible biocompatible package material to enhance safety, durability and reliability of the implantable electrical stimulator.

According to the above objectives, the present invention provides an implantable electrical stimulator, which includes: a flexible circuit board having a control circuit, a power supply circuit, a cathode conductive wire and an anode conductive wire, wherein the control circuit controls the power supply circuit to provide the cathode conductive wire and the anode conductive wire with a negative voltage and a positive voltage, respectively; a cathode electrode array having a plurality of cathode electrodes extending outward from one side of the cathode conductive wire; an anode electrode array having a plurality of anode electrodes extending outward from one side of the anode conductive wire; and a biocompatible polymer material covering the whole of the flexible circuit board and exposing portions of the cathode electrodes and the anode electrodes.

The present invention provides an implantable electrical stimulator combining a flexible circuit board, a flexible biocompatible package material and a design of electrode arrays to enlarge an electrical treatment area, improving electrical treatment efficiency, and making the implanting position and implanting way of the present electrical stimulator more flexible. Hence, the present electrical stimulator is more humanized, more widely used, and has enhancement of safety, durability and reliability after an implantable electrical stimulator is implanted to a human body.

The purposes and many advantages of the present invention are illustrated by detailed description of the embodiment, and become clearer understood with reference to accompanying drawings.

DETAILED DESCRIPTION OF THE PREFERRED EMBODIMENTS

The present invention provides an implantable electrical stimulator employing a flexible circuit board, a flexible biocompatible package material to make the implanting position and implanting way of the present electrical stimulator more flexible, and it can naturally adjust appearance based on the shapes of muscular tissue, bones and organs, in addition, due to such flexibility it has, there is hardly a discomfort after implantation, and it is hardly affected by external percussion. On the other hand, the present invention employs a design of electrode arrays to enlarge an electrical treatment area and improve electrical treatment efficiency.

To be specific, the present invention uses the technology of Flexible Printed Circuit Board, FPCB, to manufacture a circuit board having a type of wireless transmission of energy, and buries easily-conductive parts likes legs of electrical components and conductive wires on a circuit board with black epoxy (Glass Transition Temperature, Tg>60° C.) to enhance insulation, and then, uses biocompatible polymer material to cover the surface of a print circuit board and completes an implantable electrical stimulator of the present invention.

An implantable electrical stimulator of the present invention would be explained in detail by the following embodiments with reference to accompanying drawings.

Figure 1A:
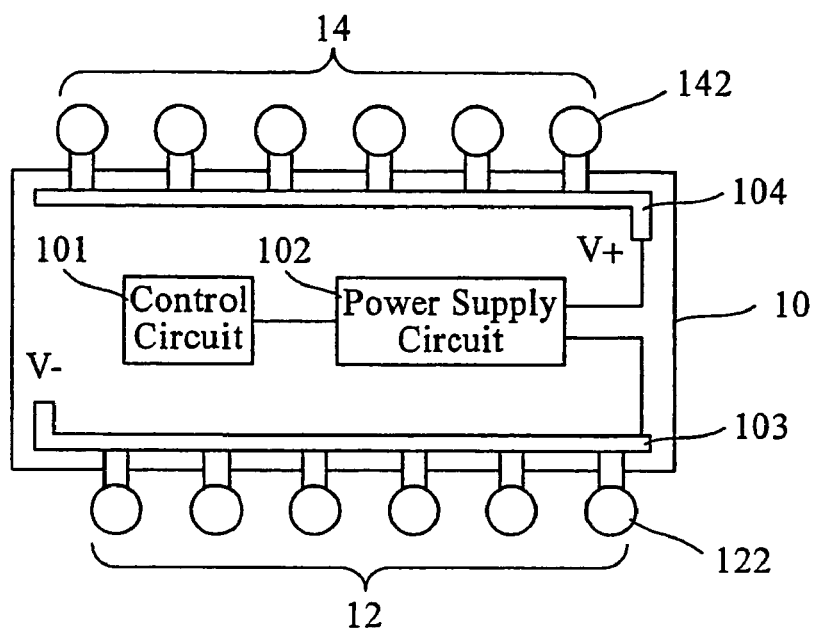
FIG. 1A to FIG. 1C is schematic top views of various manufacturing stages of a flexible implantable electrical stimulator according to a first embodiment of the present invention.
Figure 1B:
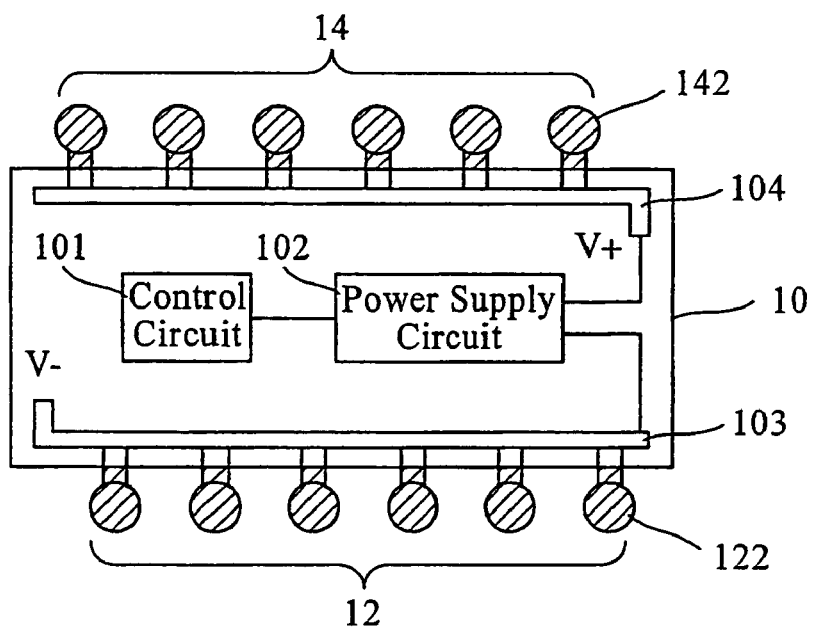
Figure 1C:
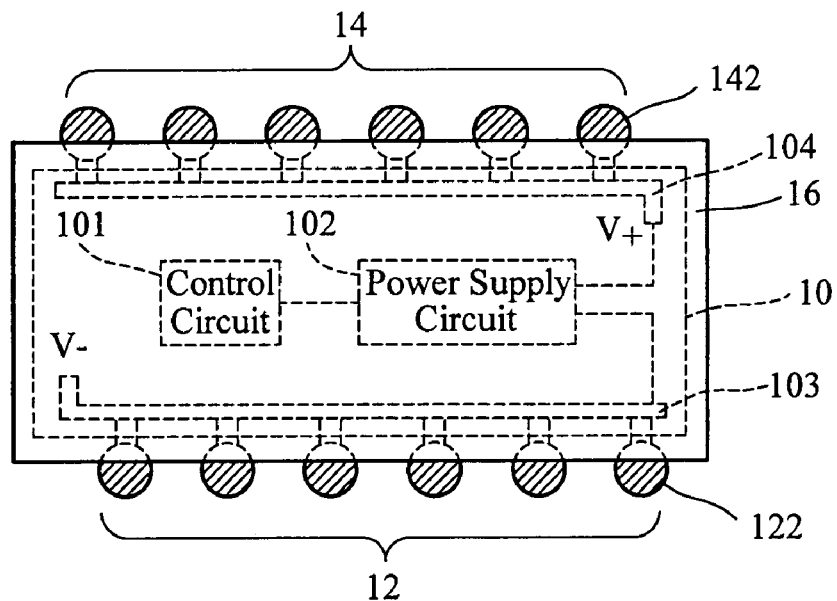

FIG. 1A to FIG. 1C is schematic top views of various manufacturing stages of a flexible implantable electrical stimulator according to a first embodiment of the present invention. See FIG. 1A, firstly, to provide a flexible circuit board 10, a flexible printed circuit board for example, which has a control circuit 101, a power supply circuit 102, a cathode conductive wire 103 and an anode conductive wire 104. The flexible implantable electrical stimulator gains energy from external by employing the method of wireless transmission of energy, such as coil induction and antenna induction, to drive the control circuit 101, and then, the control circuit 101 controls the power supply circuit 102 providing a negative voltage and a positive voltage to a cathode conductive wire 103 and an anode conductive wire 104, respectively. A cathode electrode array 12 having a plurality of cathode electrodes 122 extending outward from one side of the cathode conductive wire 103. An anode electrode array 14 having a plurality of anode electrode 142 extending outward from one side of the anode conductive wire 104.

Then, see FIG. 1B, to coat biocompatible conductive material, such as tantalum, stainless steel and titanium, on the extending parts of the cathode electrodes 122 and the anode electrode 142 from the flexible circuit board 10. Then, see FIG. 1C, using a biocompatible polymer layer 16 to cover the entire flexible circuit board 10, and only expose parts of the cathode electrode array 12 and the anode electrode array 14. The biocompatible polymer layer 16 can be silicone, PTMS (poly(tetramethylene succinaze)) and PMMA (poly(methylmethacrylaze)). Moreover, before using the biocompatible polymer layer 16 to cover the entire flexible circuit board 10, black epoxy (Glass Transition Temperature Tg>60° C.) can be used to bury electric components on the flexible circuit board, such as the connective legs of the electric components on the control circuit 101 and power supply circuit 102, the cathode conductive wire 103 and the anode conductive wire 104, to enhance insulation, and then biocompatible polymer layer 16 covers the entire flexible circuit board 10.

Figure 2:
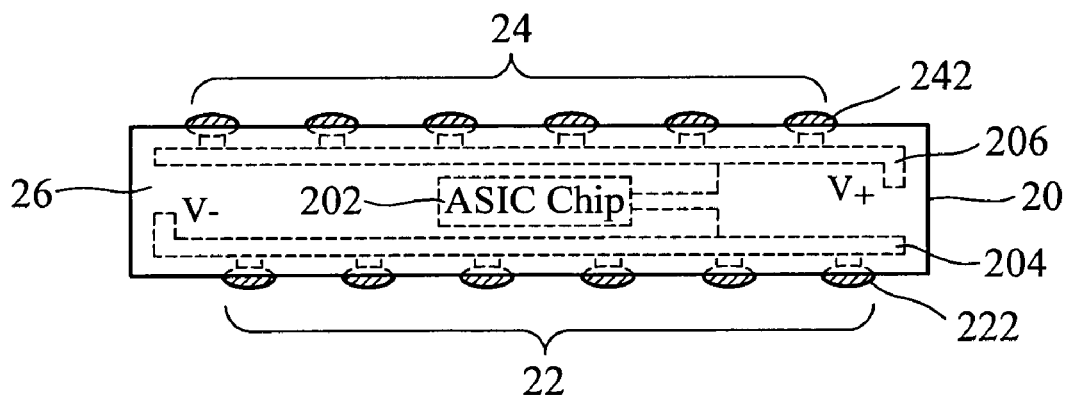
FIG. 2 is a schematic top view of a flexible implantable electrical stimulator according to a second embodiment of the present invention.

FIG. 2 is a schematic top view of a flexible implantable electrical stimulator according to a second embodiment of the present invention. In the second embodiment, the circuits on the circuit board are integrated in a single chip by the way of Application Specific Integrated Circuit, ASIC. In other words, a flexible implantable electrical stimulator of the second embodiment comprises: a flexible circuit board 20 having an ASIC chip 202, a cathode conductive wire 204 and an anode conductive wire 206, wherein the ASIC chip provides a negative voltage and a positive voltage to the cathode conductive wire 204 and the anode conductive wire 206, respectively; a cathode electrode array 22 having a plurality of cathode electrodes 222 extending outward from one side of the cathode conductive wire 204; an anode electrode array 24 having a plurality of anode electrode 242 extending outward from one side of the anode conductive wire 206; a biocompatible polymer layer 26 covering the entire flexible circuit board 20 and exposing portions of the cathode electrode array 22 and the anode electrode array 24. The flexible circuit board 20 gains electric energy from the external by employing the method of wireless transmission of energy, such as coil induction and antenna induction, to drive the ASIC chip. Then, as the same as the first embodiment, before using the biocompatible polymer layer 26 to cover the entire flexible circuit board 20, it can use black epoxy (Glass Transition Temperature Tg>60° C.) to bury electric connective legs of the electric components on the flexible circuit board 20, the cathode conductive wire 103 and the anode conductive wire 104, to enhance insulation. Then, the extending parts of the cathode electrodes 222 and the anode electrodes 242 from the flexible circuit board 20 are coated with biocompatible conductive materials, such as tantalum, stainless steel and titanium. The flexible implantable electrical stimulator of the second embodiment integrated circuits on the flexible circuit board in a single ASIC chip, and it can be used by rolling up to minimize the space of an electrical stimulator occupying the human body.

Figure 3:
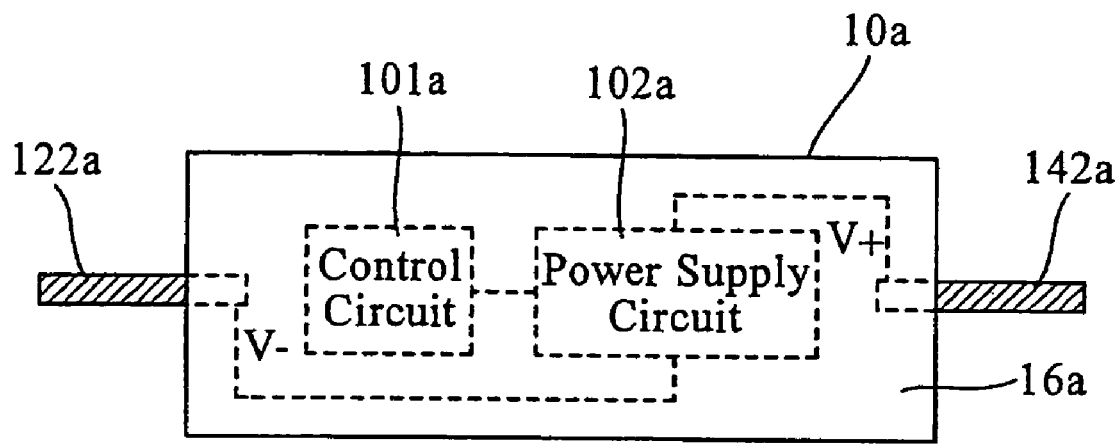
FIG. 3 is a schematic top view of a variation of the first embodiment.

FIG. 3 is a schematic top view of a variation of the first embodiment, the difference from the first embodiment is that a cathode electrode 122a and an anode electrode 142a replace the cathode electrode array 12 and the anode electrode array 14 of the first embodiment, respectively. That is, the flexible implantable electrical stimulator of the present invention shown in FIG. 3 comprises a flexible circuit board 10a, such as a flexible circuit board having a control circuit 101a, a power supply circuit 102a, a cathode electrode 122a extending outward from one side of the flexible circuit board 10a and an anode electrode 142a extending outward from the opposite side of the flexible circuit board 10a. The flexible implantable electrical stimulator gains energy from external by employing the method of wireless transmission of energy, such as coil induction and antenna induction, to drive the control circuit 101a, and then, the control circuit 101a controls the power supply circuit 102a providing a negative voltage and a positive voltage to the cathode electrode 122a and the anode electrode 142a, respectively.

The extending parts of the cathode electrodes 122a and the anode electrodes 142a from the flexible circuit board 10a are coated with the biocompatible conductive material, such as tantalum, stainless steel and titanium. A biocompatible polymer layer 16 covers the entire flexible circuit board 10a and only exposes the portions of the cathode electrode array 122a and the anode electrode array 142a. The biocompatible polymer layer 16 can be silicone, PTMS (poly(tetramethylene succinaze)) and PMMA (poly(methylmethacrylaze)). Moreover, before using biocompatible polymer layer 16a to cover the entire flexible circuit board 10a, black epoxy (Glass Transition Temperature Tg>60° C.) can bury electric components on the flexible circuit board 10a, such as the connective legs of the electric components on the control circuit 101a and power supply circuit 102a, the cathode electrode 122a and the anode electrode 142a, to enhance insulation, and then the biocompatible polymer layer 16a covers the entire flexible circuit board 10a.

Figure 4:
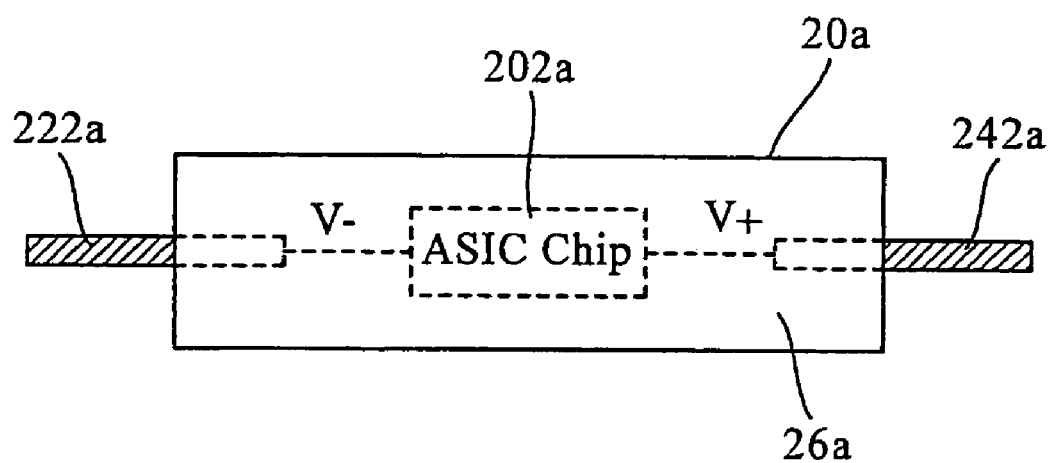
FIG. 4 is a schematic top view of a variation of the second embodiment.

FIG. 4 is a schematic top view of a variation of the second embodiment, the difference from the second embodiment is that a cathode electrode 222a and an anode electrode 242a replace the cathode electrode array 22 and the anode electrode array 24 of the second embodiment, respectively. That is, the flexible implantable electrical stimulator of the present invention shown in FIG. 4 comprises a flexible circuit board 20a having an ASIC chip 202a, a cathode electrode 222a extending outward from one side of the flexible circuit board 20a and an anode electrode 242a extending outward from the opposite side of the flexible circuit board 20a. The ASIC chip 202a provides a negative voltage and a positive voltage to the cathode electrode 222a and the anode electrode 242a, respectively. A biocompatible polymer layer 26 covers the entire flexible circuit board 20a to expose portions of the cathode electrode 222a and the anode electrode 242a. The flexible circuit board 20a gains energy from external by employing the method of wireless transmission of energy, such as coil induction and antenna induction, to drive the ASIC chip 202a. Then, as the same as the first embodiment, before using the biocompatible polymer layer 26a to cover the entire flexible circuit board 20a, black epoxy (Glass Transition Temperature Tg>60° C.) can bury connective legs of the electric components on the flexible circuit board 20a, the partial cathode electrode 222a and the partial anode electrode 242a, to enhance insulation. Then, the extending parts of the cathode electrodes 222a and the anode electrode 242a from the flexible circuit board 20a are coated with a biocompatible conductive material, such as tantalum, stainless steel and titanium.

The biocompatible materials using in the present invention meet the ISO 10993.

In conclusion, the present invention provides a kind of implantable electrical stimulator that is lighter, thinner, high circuit density, easy to process, low hygroscopic, high reliability, biocompatible, and providing enhancing electric-treatment.

Although the present invention has been described in considerable detail with reference to certain preferred embodiments thereof, those skilled in the art can easily understand that all kinds of alterations and changes can be made within the spirit and scope of the appended claims. Therefore, the spirit and scope of the appended claims should not be limited to the description of the preferred embodiments contained herein.

What is claimed is:

1. A flexible implantable electrical stimulator array, comprising:
   a flexible circuit board having a control circuit, a power supply circuit, a cathode conductive wire and an anode conductive wire, wherein said control circuit controls said power supply circuit to provide said cathode conductive wire and said anode conductive wire with a negative voltage and a positive voltage, respectively;
   a cathode electrode array having a plurality of cathode electrodes extending outward from one side of said cathode conductive wire;
   an anode electrode array having a plurality of anode electrodes extending outward from one side of said anode conductive wire; and
   a biocompatible polymer material covering the whole of said flexible circuit board and exposing portions of said cathode electrodes and said anode electrodes,
   wherein said cathode and anode electrode arrays extend outward from opposite lateral sides of said flexible circuit board.

2. The flexible implantable electrical stimulator array as defined in claim 1, wherein said flexible circuit board gains electric energy from the external by wireless transmission of energy to drive said control circuit.

3. The flexible implantable electrical stimulator array as defined in claim 1, wherein the wireless transmission of energy is realized by the following methods: coil induction and antenna induction.

4. The flexible implantable electrical stimulator array as defined in claim 1, wherein comprising a black epoxy for covering electric components of said control circuit and said power supply circuit as well as said cathode electrode and said anode electrode.

5. The flexible implantable electrical stimulator array as defined in claim 1, wherein the exposed portions of said cathode electrode and said anode electrode are covered by a biocompatible conductive material.

6. The flexible implantable electrical stimulator array as defined in claim 5, wherein said biocompatible conductive material is selected from a group consisting of the following: tantalum, stainless steel and titanium.

7. The flexible implantable electrical stimulator array as defined in claim 1, wherein said biocompatible polymer layer is selected from a group consisting of the following: silicone, PTMS (poly(tetramethylene succinaze)) and PMMA (poly(methylmethacrylaze)).

8. The flexible implantable electrical stimulator array as defined in claim 5, wherein said biocompatible polymer layer is selected from a group consisting of the following: silicone, PTMS (poly(tetramethylene succinaze)) and PMMA (poly(methylmethacrylaze)).

9. The flexible implantable electrical stimulator array as defined in claim 1, wherein said control circuit and said power supply control circuit are integrated in an ASIC chip.

10. The flexible implantable electrical stimulator array as defined in claim 9, wherein said biocompatible polymer layer is selected from a group consisting of the following: silicone, PTMS (poly(tetramethylene succinaze)) and PMMA (poly(methylmethacrylaze)).

* * * * *